United States Patent
Wang et al.

(10) Patent No.: US 12,168,210 B2
(45) Date of Patent: Dec. 17, 2024

(54) DEVICES, SYSTEMS, AND METHODS OF ELECTRONIC MODULATION OF POLYMERASE FOR DNA SYNTHESIS

(71) Applicant: Georgia Tech Research Corporation, Atlanta, GA (US)

(72) Inventors: Hua Wang, Atlanta, GA (US); Andrew Hessel, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 366 days.

(21) Appl. No.: 17/055,803

(22) PCT Filed: May 17, 2019

(86) PCT No.: PCT/US2019/032844
§ 371 (c)(1),
(2) Date: Nov. 16, 2020

(87) PCT Pub. No.: WO2019/222612
PCT Pub. Date: Nov. 21, 2019

(65) Prior Publication Data
US 2021/0229059 A1  Jul. 29, 2021

Related U.S. Application Data

(60) Provisional application No. 62/672,660, filed on May 17, 2018.

(51) Int. Cl.
*B01J 19/00* (2006.01)
*C40B 50/14* (2006.01)

(52) U.S. Cl.
CPC ........... *B01J 19/0046* (2013.01); *C40B 50/14* (2013.01); *B01J 2219/00596* (2013.01); *B01J 2219/00626* (2013.01); *B01J 2219/00653* (2013.01); *B01J 2219/00659* (2013.01); *B01J 2219/00673* (2013.01); *B01J 2219/00689* (2013.01); *B01J 2219/00713* (2013.01)

(58) Field of Classification Search
None
See application file for complete search history.

(56) References Cited

U.S. PATENT DOCUMENTS

| | | | |
|---|---|---|---|
| 2019/0080760 A1* | 3/2019 | Predki | .................... G06N 3/123 |
| 2019/0136309 A1* | 5/2019 | Church | ................ C12Q 1/6869 |

OTHER PUBLICATIONS

Yue et al (Current Protocols in Molecular Biology 3.6.1-3.6.3) (Year: 2008).*
McCarthy et al (J. Mol. Biol. 106:963-81) (Year: 1976).*

* cited by examiner

*Primary Examiner* — Christopher M Gross
(74) *Attorney, Agent, or Firm* — Troutman Pepper Hamilton Sanders LLP; Ryan A. Schneider; Chris N. Davis

(57) ABSTRACT

A method of synthesis of a nucleotide chain, the nucleotide chain including an ordered plurality of nucleotides, the method including: identifying a first nucleotide of the ordered plurality of nucleotides; controlling a polymerase enzyme to assemble the first nucleotide onto the nucleotide chain by electrically modulating an electrode; identifying a subsequent nucleotide in the ordered plurality of nucleotides as a current nucleotide; and controlling the polymerase enzyme to assemble the current nucleotide onto an end of the nucleotide chain by electrically modulating the electrode.

12 Claims, 7 Drawing Sheets

DEVICES, SYSTEMS, AND METHODS OF ELECTRONIC MODULATION OF POLYMERASE FOR DNA SYNTHESIS

CROSS REFERENCE TO RELATED APPLICATIONS

This application claims priority to U.S. Provisional Patent Application Ser. No. 62/672,660, filed on May 17, 2018, which is incorporated herein by reference in its entirety.

FIELD

This disclosure relates generally to the nucleic acid compilation and, more specifically, to devices, systems, and methods of electronic modulation of polymerase for DNA synthesis.

BACKGROUND

Deoxyribonucleic acid (DNA) molecules are the carriers of genetic information of all known living organisms and govern their growth, development, functioning and reproduction. In recent years, advances in the field of genomics have led to continuous improvement of high throughput DNA sequencing techniques, e.g., Next-Generation-Sequencing (NGS), and resulted in a steep reduction in the cost of genome sequencing. However, compared to DNA sequencing, the de novo synthesizing of DNA molecules (i.e., designed sequences) has lagged significantly. As used herein, de novo DNA synthesis (hereafter "DNA synthesis" or "de novo DNA synthesis") refers to creating nucleic acid sequences with designed genetic information without using any primer or template DNAs. In other words, de novo DNA synthesis does not include DNA replication/amplification techniques such as PCR that rely on existing templates.

In the related art, de novo DNA syntheses is a multi-step process including: 1) synthesizing pools of small oligonucleotide ("oligo") fragments; 2) verifying the sequences of the small fragments; 3) assembling the fragments to create a complete DNA sequence; and 4) sequence verifying the complete sequence. As will be understood by one of ordinary skill, in the related art, oligo fragment synthesis relies heavily on direct phosphoramidite chemistry, such as solid-phase column-based oligo synthesis and microarray-based oligo light-activated synthesis. However, these related art oligo fragment synthesis have significant error rates, which limits the practical size of the oligos. Thus, while related art DNA synthesis technologies have been used for construction of viral genomes and yeast chromosomal arms, the successive assembly-sequence validation process becomes onerous as the chain length increases, substantially increasing cost and turnaround times. For example, employing one of the lowest-cost related art oligo synthesis methods at $1 per 1,000 base pairs, even assuming perfect oligo assembly with no assembly cost, synthesizing a whole human genome of 3 billion base pairs will cost over $3 million, which is over 3,000 times as expensive as sequencing an entire human genome. More realistic estimates (e.g., including assembly costs) could raise this orders of magnitude higher, likely between $100M and $1B, while the turnaround time would be several years. That is, related art chemical synthesis has assembly rates of, at best, about 1 base pair per minute. These technical limitations make the synthesis of large genomes impractical.

Thus, there is an unmet need for improvements to de novo DNA synthesis that reduce the cost and increase speed. Aspects of the present disclosure relate to these and other issues.

SUMMARY

The disclosed technology provides systems, devices, and methods for electronic manipulation of polymerase for DNA synthesis. Although this disclosure focuses on DNA synthesis, those having ordinary skill in the art will recognize that the systems, devices, and techniques described herein are not so limited and may be suitably applied across a wide array of uses, such as RNA synthesis.

In an embodiment, there is provided a method of synthesis of a nucleotide chain, the nucleotide chain including an ordered plurality of nucleotides, the method comprising including: identifying a first nucleotide of the ordered plurality of nucleotides; controlling a polymerase enzyme to assemble the first nucleotide onto the nucleotide chain by electrically modulating an electrode; identifying a subsequent nucleotide in the ordered plurality of nucleotides as a current nucleotide; and controlling the polymerase enzyme to assemble the current nucleotide onto an end of the nucleotide chain by electrically modulating the electrode.

In an embodiment, there is provided a system including: an electrode; a polymerase enzyme immobilized adjacent to the electrode; and a processor; and a memory having stored thereon instructions that, when executed by the processor, control the processor to electrically modulate the electrode to control the polymerase enzyme to assemble a nucleotide chain, the nucleotide chain comprising an ordered plurality of nucleotides. The instructions, when executed by the processor, may further control the processor to: identify a first nucleotide of the ordered plurality of nucleotides; control the polymerase enzyme to assemble the first nucleotide onto the nucleotide chain by electrically modulating an electrode; identify a subsequent nucleotide in the ordered plurality of nucleotides as a current nucleotide; and control the polymerase enzyme to assemble the current nucleotide onto an end of the nucleotide chain by electrically modulating the electrode.

According to an embodiment, there is provided a non-transitory computer readable medium comprising program instructions for performing a method of a nucleotide chain, the nucleotide chain including an ordered plurality of nucleotides, the method comprising including: identifying a first nucleotide of the ordered plurality of nucleotides; controlling a polymerase enzyme to assemble the first nucleotide onto the nucleotide chain by electrically modulating an electrode; identifying a subsequent nucleotide in the ordered plurality of nucleotides as a current nucleotide; and controlling the polymerase enzyme to assemble the current nucleotide onto an end of the nucleotide chain by electrically modulating the electrode.

BRIEF DESCRIPTION OF THE FIGURES

Reference will now be made to the accompanying Figures, which are not necessarily drawn to scale, and wherein.

DETAILED DESCRIPTION

Figure 1:
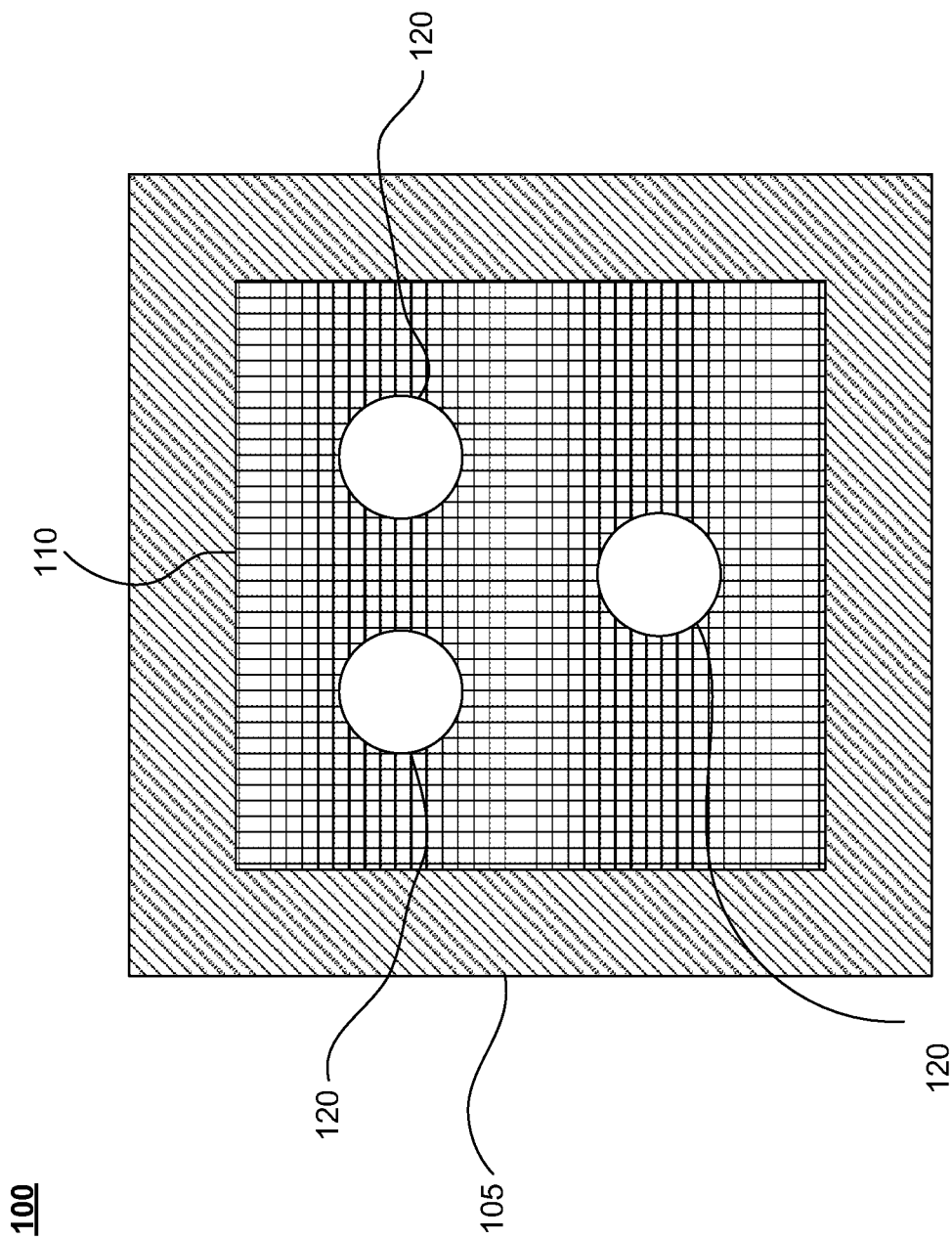
FIG. 1 illustrates a planar view of an electrode platform according to an example embodiment.

Some implementations of the disclosed technology will be described more fully with reference to the accompanying drawings. This disclosed technology may, however, be embodied in many different forms and should not be construed as limited to the implementations set forth herein.

According to some aspects of the present disclosure, there is provided a polymerase enzyme, such as a template independent DNA polymerase, immobilized near an electrode. By applying electric modulation (e.g., varying voltage biasing of the electrode), the polymerase may be controlled to build selectable or programmable strands of nucleic acids (e.g., DNA or RNA), for example, up-to and including an entire genome. In other words, synthesis of an ordered nucleotide chain segment may be performed using polymerase enzymes. The polymerase may be immobilized by, for example, bonding the polymerase to a surface of microelectrode or leashing the polymerase to the electrode with a polyethylene glycol (PEG) chain. In some cases, a plurality of polymerase enzymes may be bonded to one or more respective electrodes of a microelectrode array, and selective electric modulation of each electrode may provide parallel construction of plurality of nucleic acid strands.

Polymerases naturally assemble base pairs at very high speeds as compared to chemical synthesis, about 1000 base pairs per second (bp/s), which is over 60,000 the speed of chemical synthesis. Thus, a single polymerase could assemble a full 3 billion bp DNA strand in a matter of weeks, as opposed to the years of assembly time required using related art methods. By using a plurality of polymerase to synthesize DNA fragments in parallel for later assembly, DNA synthesis may be accelerated even further beyond what is possible in the related art.

As will be understood by one of ordinary skill, aspects of the present disclosure provide numerous advantages over the related art. For example, improved methods of DNA synthesis may provide a new, fundamental molecular-level tool and method for genetic studies, such as constructing comprehensive and bar-coded knockout genetic libraries for human cell lines. Additionally, de novo DNA synthesis as described herein may facilitate understanding on the structural and functional characteristics of thousands of regulatory sequences and help delineate the roles of these sequences in governing transcriptional, translational and other regulatory processes in various biological systems. Furthermore, aspects of the present disclosure provide low cost, rapid DNA (gene) synthesis, which enables rational protein design, studying of protein structure-function relationships, and the engineering new protein functionalities, vaccines and antibiotics. Likewise, large-scaled de novo DNA synthesis as provided by certain aspects of the present disclosure can greatly accelerate the "design-build-test-learn" cycle in synthetic biology, allowing for rapid building and optimizing genetic networks to control cellular behaviors and metabolic pathways (e.g., for chemical productions or cell-based chemical sensing). Furthermore, de novo synthesis DNAs at genome level complexity enable the complete control of an organism's genetic code, providing for the complete rational design and synthesis of viral and bacterial. Such de novo DNA synthesis can also greatly facilitate the utilization of DNA as a molecular tool to create complex 2D and 3D structures for new materials and therapeutics and to perform information processing and computation. As another benefit, low-cost long-sequence de novo DNA synthesis according to aspects of the present disclosure empowers DNA-based high-density data storage and archiving.

Although aspects of the present disclosure are generally described in reference to a DNA polymerase (e.g., a template-independent DNA polymerase, such as a Taq DNA polymerase), this is merely an example. One of ordinary skill will recognize that aspects of the present disclosure are applicable to use with an RNA polymerase.

Example implementations of the disclosed technology will now be described with reference to the accompanying figures.

FIG. 1 illustrates a planar view of an electrode platform 100 according to an example embodiment. The electrode platform 100 includes a substrate 105, an electrode 110, and one or more links 120 for immobilizing an enzyme at electrode 110. The links 120 may include, for example, biotin-streptavidin links which are configured to attach to an enzyme such as a polymerase. In some cases, a PEG chain may secure the polymerase near electrode 110, while allowing the enzyme to "float" or more easily adjust to electric modulation. By modulating power supplied to the electrode 110 and/or surrounding electrodes, a functioning of the enzyme may be controlled.

For example, the enzyme connected to the links 120 may be a DNA polymerase, such as a template-independent DNA polymerase. As will be understood by one of ordinary skill, template-independent DNA polymerase catalyze the incorporation of deoxynucleotides at a terminus of a DNA strand without the use of a template (i.e., without copying an existing strand). However, this is merely an example, and in some cases, other polymerase enzymes may be used (e.g., those that typically depend on a template), but may be likewise modulated to control nucleic order. According to aspects of the present disclosure, a DNA strand may be designed and built by electric modulation to the electrode 110, thereby controlling a next nucleotide to be added to the strand. For example, the electrode 110 may have various power (e.g., between −1 V and 1.5 V) which can control functioning of the polymerase. In some situations, the sequence of electric modulation (e.g., rapidly changing voltage of the electrode 110) may be used to control the polymerase. In the case of DNA, four or more different and/or distinct electric modulations (e.g., voltage or voltage orders) may be applied to electrode 110 and/or surround electrodes to control the DNA polymerase to selective add adenine (A), thymine (T), guanine (G), or cytosine (C) as a next nucleotide in a DNA strand. In this way DNA strands may be programmatically built.

Figure 2:
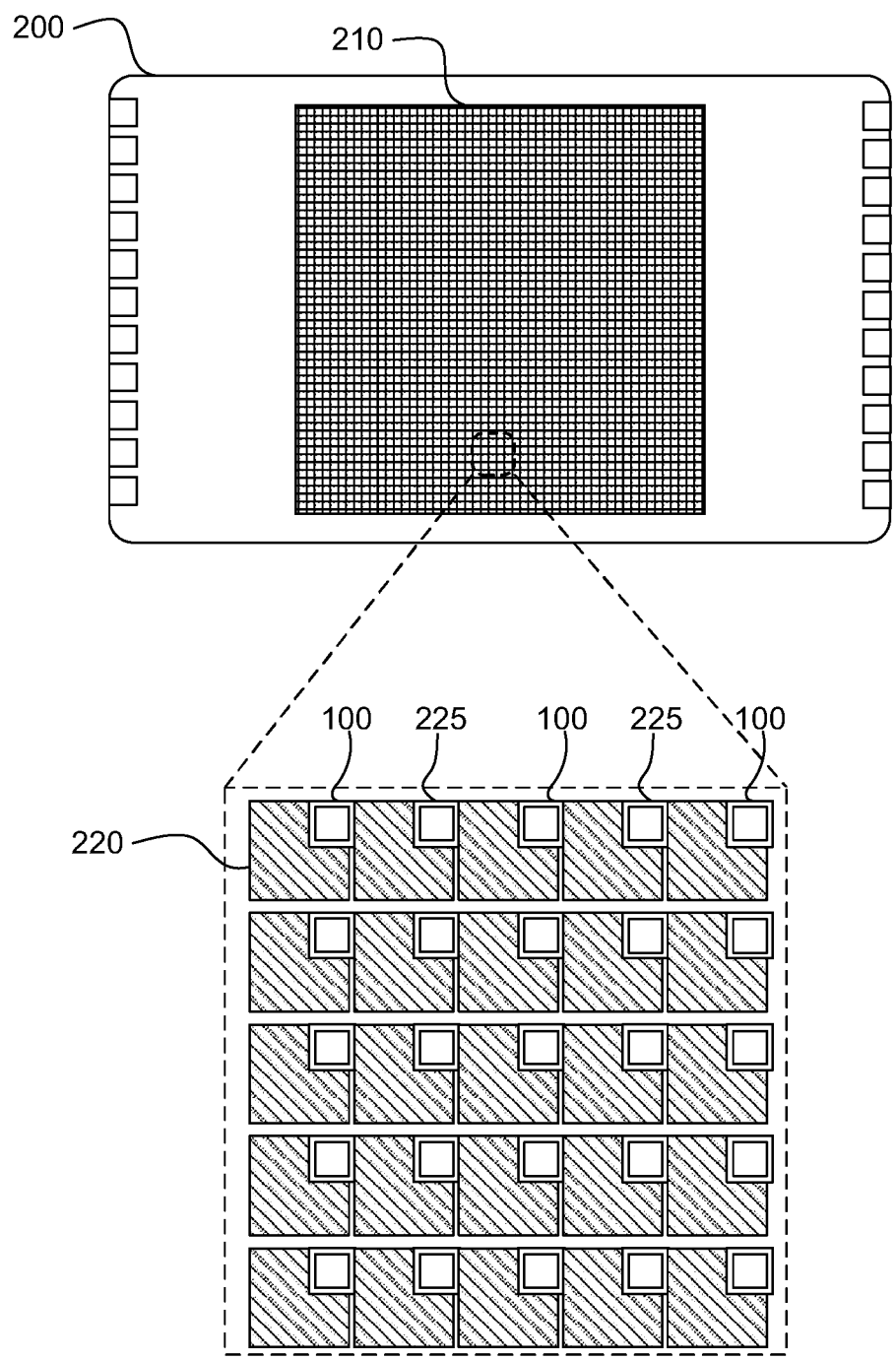
FIG. 2 illustrates an electronic array chip according to an example embodiment.

FIG. 2 illustrates an electronic array chip 200 with an electrode array 210 according to an example embodiment. The electrode array 200 may be, as non-limiting examples, a biocompatible liquid crystal polymer (LCP)-based board-level electrode array or a Complementary metal-oxide-semiconductor (CMOS)-based integrated circuit (IC)-level electrode array. One of ordinary skill will recognize that LCP is a biocompatible substrate material with high interfacial adhesion and a low degree of moisture absorption, which enhances long-term viability of microelectrodes on LCP substrates. The electronic array chip 200 may provide high-precision control of biasing voltage for each electrode individually or in parallel.

The electrode array 210 includes an array of cells 220. Each cell includes an electrode 100 or 225. Each electrode 100 may be substantially similar to that described above with reference to FIG. 1. Meanwhile, each electrode 225 may be a ground. Power provided to electrode 100 flows to ground electrodes 225 creating a programmable biasing electric field. The electric field modulates the polymerase connected to electrode 110. In some cases, electrode 225 may be selectively a voltage source or a ground to enable further modification of the electrical field.

In some cases, one or more light sources (e.g., laser light sources) directed toward the electrode 110 may be provided. The light source(s) may be activated to provide optical modulation (i.e., instead of or in addition to electric modulation of electrode 110) to modify the operation of the polymerase 130.

Figure 3:
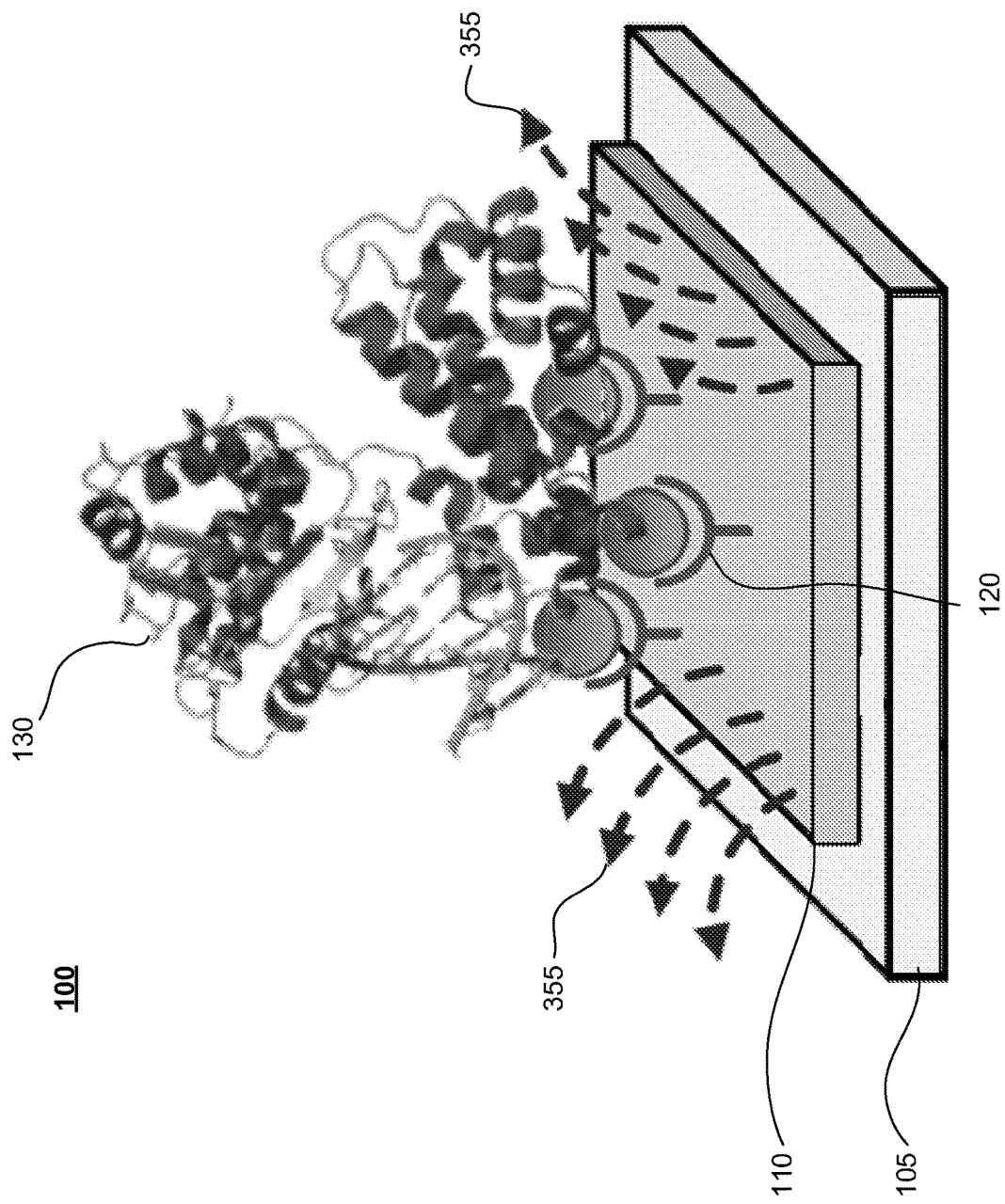
FIG. 3 is a perspective view of an electrode platform according to an embodiment.

FIG. 3 is a perspective view of an electrode platform 100 according to an embodiment. Electrode array 100 includes substrate 104, electrode 110, and bio-links 120, which may be substantially similar to like elements described above with reference to FIG. 1. Polymerase enzyme 130 is connected to the one or more of bio-links 120. FIG. 3 further depicts a programmable biasing electrical field 355 that controls polymerase enzyme 130.

Although as illustrated in FIG. 3, a single enzyme 130 is attached in a plurality of points (120) to a single electrode 110, this is merely an example. In some cases, a plurality of enzymes 130 may be attached to a single electrode 110, e.g., to facilitate creation of multiple copies of a DNA strand or fragment simultaneously. Additionally, in certain embodiments, a single enzyme 130 may be attached/tethered to/surrounded by a plurality of electrodes 110 (e.g., neighboring electrodes 110 in an array 210 forming a box or partial box). Under some circumstances, by connecting/surrounding a single enzyme 130 with a plurality of electrodes 110, the enzyme 130 may be more particularly controlled to produce a desired DNA strand with greater precision.

Figure 4:
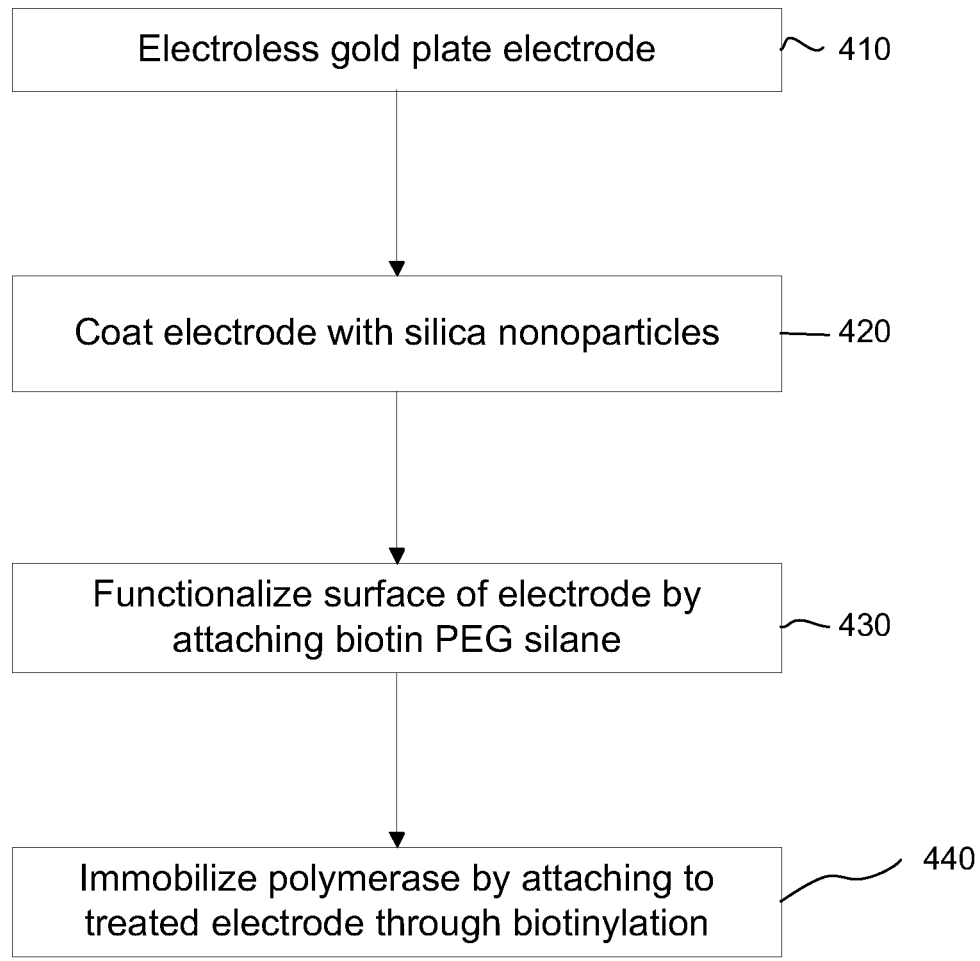
FIG. 4 is a flowchart of a method of creating an electrode platform 100 according to an embodiment.

FIG. 4 is a flowchart 400 of a method of creating an electrode platform 100 according to an embodiment. The method includes plating 400 an electrode 110 with gold. For example, plating 100 may be electroless gold plating. In some cases, a secondary plating step may be performed (e.g., with autocatalytic gold deposition) to thicken the gold layer. The gold deposition layer provides a substantially inert surface to limit unintended chemical reactions, such as with the polymerase enzyme and with the additional layers.

Next, the gold-plated electrode 110 may be coated 420 with silica nanoparticles. For example, silica nanoparticles may be applied to the electrode 110 through a self-assembled monolayer of (3-mercaptopropyl) trimethoxysilane. In some cases, the monolayer may serve as a seeding layer for depositing a thin-film sol-gel silica layer and/or an organosilane layer.

The silica-coated surface of electrode 110 is then functionalized 430 by attaching bio-links to thereto. For instance, biotin PEG silane provides functionalizes 430 the electrode 110 surface and provides bio-links 120 for enzyme attachment. Polymerase 130 is then immobilized 440 by attaching the polymerase to the treated electrode 110 through biotinylation.

One of ordinary skill will recognize that the electrode platform creation described in reference to FIG. 4 is merely an example, and various alternative techniques may be used to immobilize polymerase on an electrode.

One of ordinary skill will also recognize that improperly binding polymerase enzymes to the surface of electrode 110 may result in inhibitory activities against the effective sensing/actuation range of the surface, e.g., surface "Debye length" decrease due to attached molecules. Furthermore, non-specific binding often cannot guarantee the proper orientation of the enzyme molecules and then degrade activities and functionalities of the enzyme after immobilization. Therefore, it is essential to employ reliable polymerase immobilization techniques (such as that described above with reference to FIG. 4) that are compatible with electrodes and/or electrode arrays.

Figure 5:
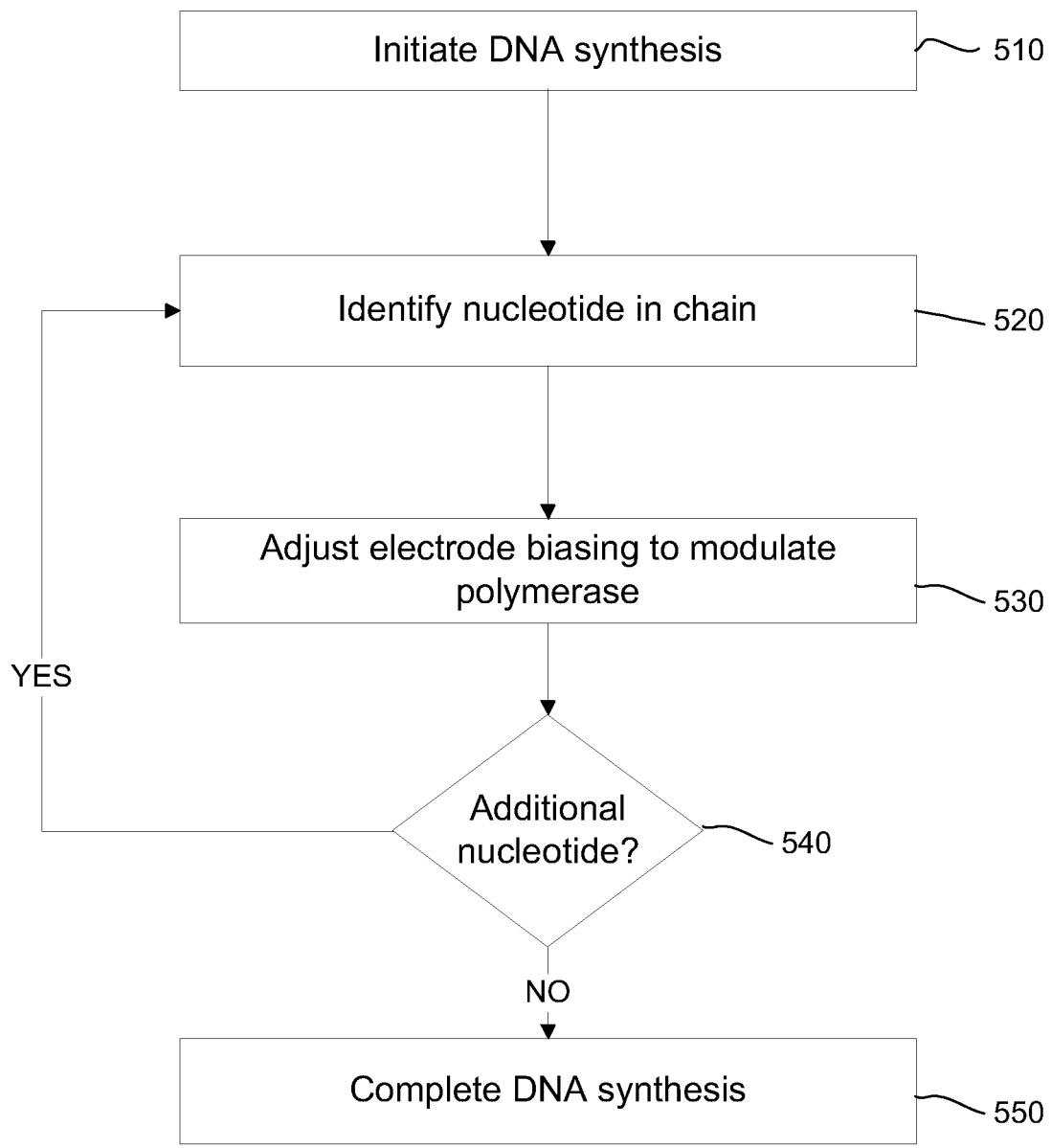
FIG. 5 is a flowchart of a method of DNA synthesis according to an embodiment.

FIG. 5 is a flowchart 500 of a method of de novo DNA synthesis according to an embodiment. The method includes initiating 510 DNA synthesis. In some cases, initiating 510 DNA synthesis may include controlling the polymerase 130 (e.g., through electrical modulation) to build a telomere. Then, a first nucleotide is identified 520. For example, data representative of a DNA strand may be provided to a processor, and the processor may identify 520 a next nucleotide in the DNA strand. Electrode 110 is adjusted to modulate 530 the polymerase 130 to add the first nucleotide to the DNA strand. For example, by adjusting the voltage biasing of the electrode 110, the polymerase may be modulated 530 to attach a different base to the end of the DNA strand.

It is determined 540 whether additional nucleotides should be added to the DNA strand. If so (540—Yes), the next or subsequent nucleotide is identified 520 and the electrode 110 is modulated 530 to add the next nucleotide to the strand. In not (540—No), DNA synthesis is completed 550. In some cases, completing 550 DNA synthesis may include controlling the polymerase 130 (e.g., through electrical modulation) to build a telomere on the end of the DNA strand.

In certain cases, DNA synthesis (e.g., as described above) may be used to create a plurality of DNA fragments. The fragments may be created sequentially (e.g., using a same electrode 110) or in parallel (e.g., using a plurality of electrodes 110). The fragments may be combined, for example, using fragment assembly techniques known in the related art, to form a complete DNA strand. Accordingly, the speed of assembly may be even further improved over the related art.

In some instances, DNA synthesis may occur within a solution (such as a solution of nucleoside triphosphate (dNTP) and/or magnesium chloride (e.g., 10 μM of dNTPs and/or 1.5 μM of $MgCl_2$)). In some instances, there may also be a reaction buffer present in the solution. As a non-limiting example, the solution may include 1.5 μM $MgCl_2$, standard PCR reaction buffer, and 10 μM of corresponding dNTPs.

Figure 6:
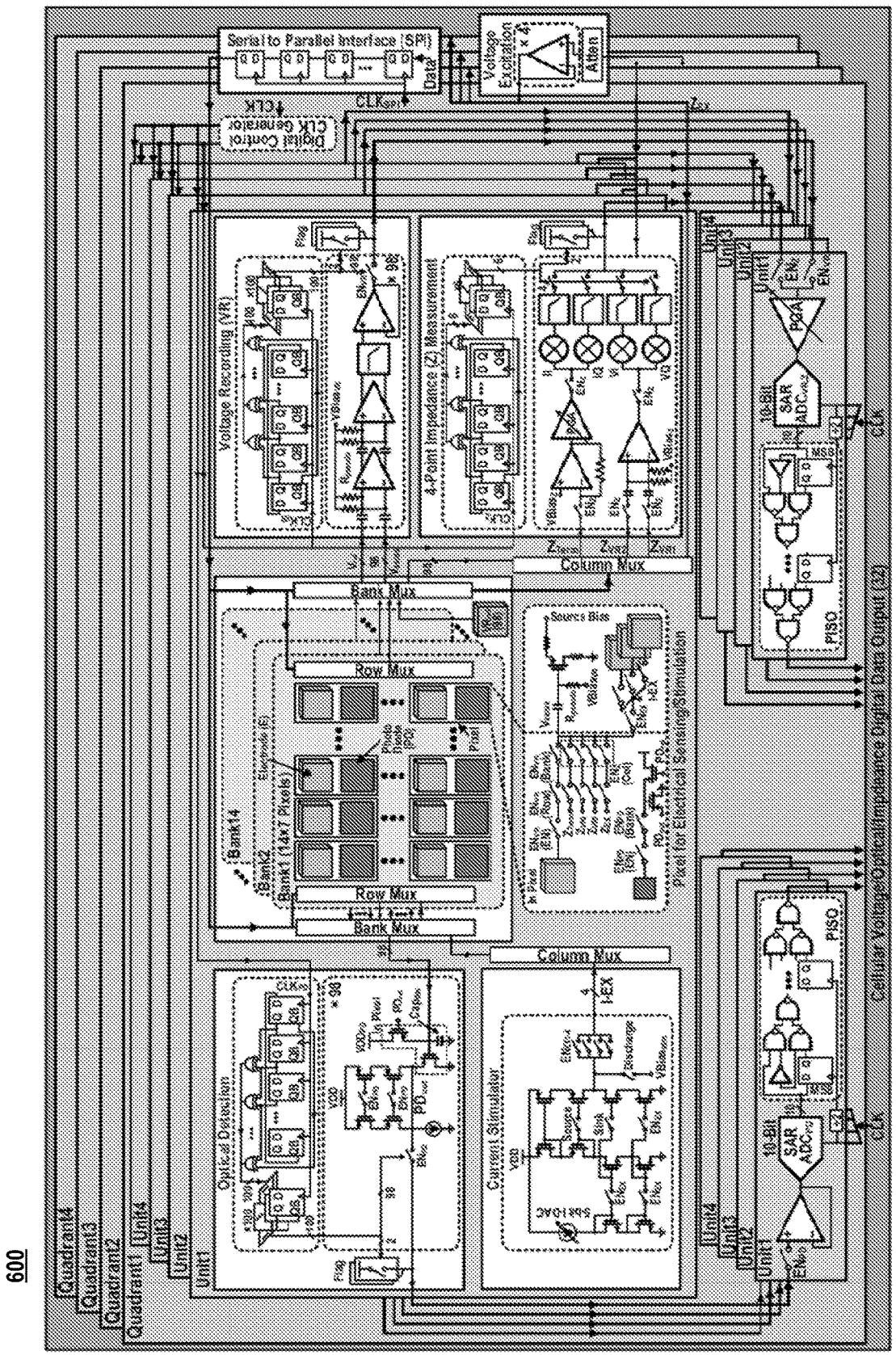
FIG. 6 is a detailed diagram of a CMOS actuation array that may be used to implement aspects of the present disclosure.

FIG. 6 is a detailed diagram of a CMOS actuation array 600 that may be used to implement aspects of the present disclosure. For example, CMOS actuation array 600 may be used as electronic array chip 200. One of ordinary skill will recognize that various alterations and alternative arrays could be utilized with aspects of the present disclosure.

Figure 7:
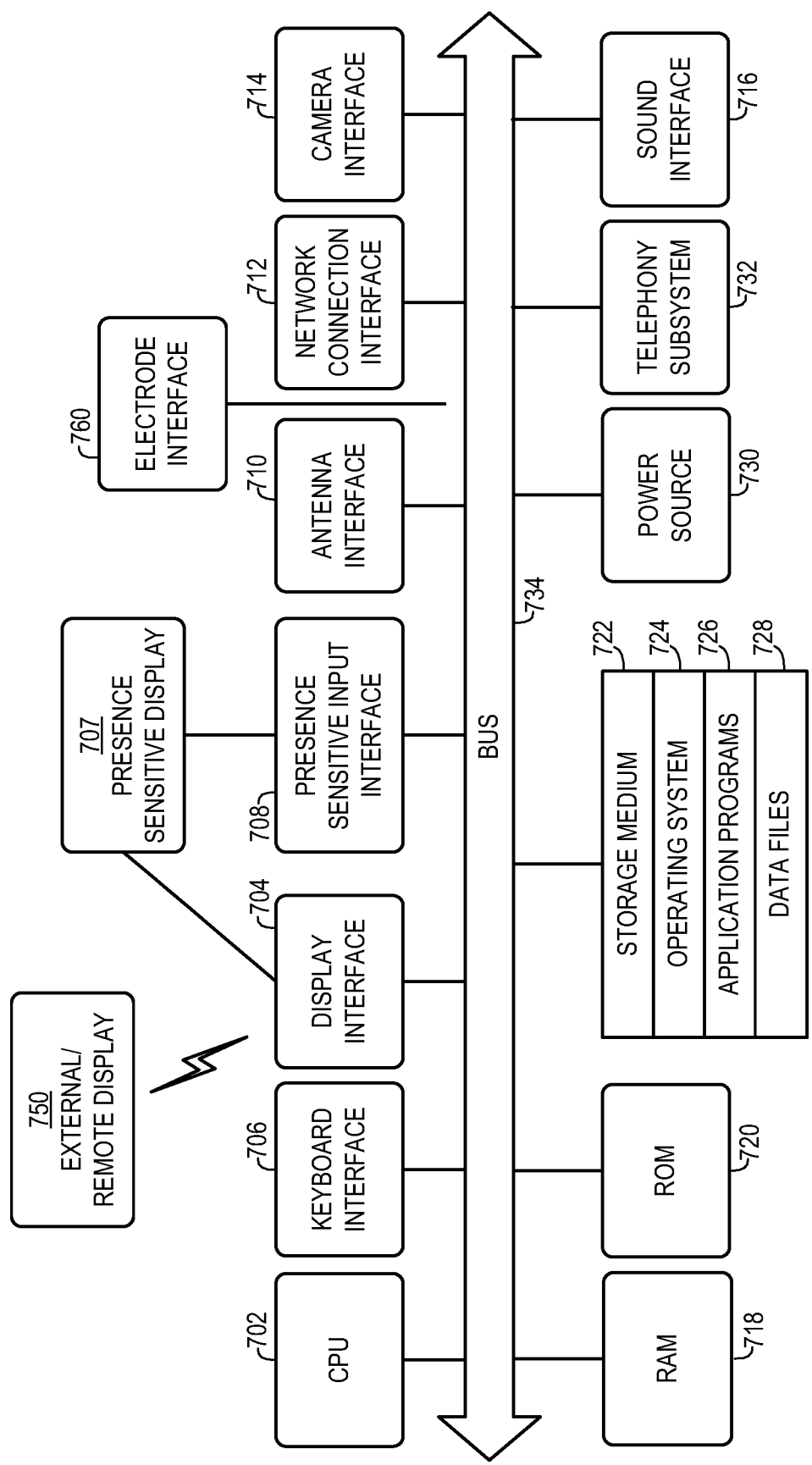
FIG. 7 illustrates a computer architecture that may implement aspects of the present disclosure.

As desired, implementations of the disclosed technology may include a computing device that can control one or more electrodes 110 with more or less of the components illustrated in FIG. 7. The computing device architecture 700 is provided for example purposes only and does not limit the scope of the various implementations of the present disclosed computing systems, methods, and computer-readable mediums.

The computing device architecture 700 of FIG. 7 includes a central processing unit (CPU) 702, where executable computer instructions are processed; a display interface 704 that supports a graphical user interface and provides functions for rendering video, graphics, images, and texts on the display. Computing device architecture 700 may include an electrode interface 760 that can connect to one or more electrodes 110 (e.g., electrode array(s) 210 and/or electronic array chip(s) 200) to monitor and/or control the same. For example, CPU 702 may control voltage biasing of the electrodes 110 to modulate polymerase 130 and control DNA synthesis. In certain example implementations of the disclosed technology, the display interface 704 connects directly to a local display, such as a touch-screen display associated with a mobile computing device. In another example implementation, the display interface 704 provides data, images, and other information for an external/remote display 750 that is not necessarily physically connected to the mobile computing device. For example, a desktop monitor can mirror graphics and other information presented on a mobile computing device. In certain example implementations, the display interface 704 wirelessly communicates, for example, via a Wi-Fi channel or other available network connection interface 712 to the external/remote display.

In an example implementation, the network connection interface 712 can be configured as a wired or wireless communication interface and can provide functions for rendering video, graphics, images, text, other information, or any combination thereof on the display. In one example, a communication interface can include a serial port, a parallel port, a general purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof.

The computing device architecture 700 can include a keyboard interface 706 that provides a communication interface to a physical or virtual keyboard. In one example implementation, the computing device architecture 700 includes a presence-sensitive display interface 708 for connecting to a presence-sensitive display 707. According to certain example implementations of the disclosed technology, the presence-sensitive input interface 708 provides a communication interface to various devices such as a pointing device, a capacitive touch screen, a resistive touch screen, a touchpad, a depth camera, etc. which may or may not be integrated with a display.

The computing device architecture 700 can be configured to use one or more input components via one or more of input/output interfaces (for example, the keyboard interface 706, the display interface 704, the presence sensitive input interface 708, network connection interface 712, camera interface 714, sound interface 716, etc.) to allow the computing device architecture 700 to present information to a user and capture information from a device's environment including instructions from the device's user. The input components can include a mouse, a trackball, a directional pad, a track pad, a touch-verified track pad, a presence-sensitive track pad, a presence-sensitive display, a scroll wheel, a digital camera including an adjustable lens, a digital video camera, a web camera, a microphone, a sensor, a smartcard, and the like. Additionally, an input component can be integrated with the computing device architecture 700 or can be a separate device. As additional examples, input components can include an accelerometer, a magnetometer, a digital camera, a microphone, and an optical sensor.

Example implementations of the computing device architecture 700 can include an antenna interface 710 that provides a communication interface to an antenna; a network connection interface 712 can support a wireless communication interface to a network. As mentioned above, the display interface 704 can be in communication with the network connection interface 712, for example, to provide information for display on a remote display that is not directly connected or attached to the system. In certain implementations, a camera interface 714 is provided that acts as a communication interface and provides functions for capturing digital images from a camera. In certain implementations, a sound interface 716 is provided as a communication interface for converting sound into electrical signals using a microphone and for converting electrical signals into sound using a speaker. According to example implementations, a random access memory (RAM) 718 is provided, where executable computer instructions and data can be stored in a volatile memory device for processing by the CPU 702.

According to an example implementation, the computing device architecture 700 includes a read-only memory (ROM) 720 where invariant low-level system code or data for basic system functions such as basic input and output (I/O), startup, or reception of keystrokes from a keyboard are stored in a non-volatile memory device. According to an example implementation, the computing device architecture 700 includes a storage medium 722 or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), for storing files include an operating system 724, application programs 726 (including, for example, a web browser application, a widget or gadget engine, and or other applications, as necessary), and data files 728. According to an example implementation, the computing device architecture 700 includes a power source 730 that provides an appropriate alternating current (AC) or direct current (DC) to power components.

According to an example implementation, the computing device architecture 700 includes a telephony subsystem 732 that allows the device 700 to transmit and receive audio and data information over a telephone network. Although shown as a separate subsystem, the telephony subsystem 732 may be implemented as part of the network connection interface 712. The constituent components and the CPU 702 communicate with each other over a bus 734.

According to an example implementation, the CPU 702 has appropriate structure to be a computer processor. In one arrangement, the CPU 702 includes more than one processing unit. The RAM 718 interfaces with the computer bus 734 to provide quick RAM storage to the CPU 702 during the execution of software programs such as the operating system, application programs, and device drivers. More specifically, the CPU 702 loads computer-executable process steps from the storage medium 722 or other media into a field of the RAM 718 in order to execute software programs. Data can be stored in the RAM 718, where the data can be accessed by the computer CPU 702 during execution. In one example configuration, the device architecture 700 includes at least 728 MB of RAM, and 256 MB of flash memory.

The storage medium 722 itself can include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media allow a computing device to access computer-executable process steps, application programs and the like, stored on removable and non-removable memory media, to off-load data from the device or to upload data onto the device. A computer program product, such as one utilizing a communication system, can be tangibly embodied in storage medium 722, which can include a machine-readable storage medium.

According to one example implementation, the term computing device, as used herein, can be a CPU, or conceptualized as a CPU (for example, the CPU 702 of FIG. 7). In this example implementation, the computing device (CPU) can be coupled, connected, and/or in communication with one or more peripheral devices, such as display. In another example implementation, the term computing device, as used herein, can refer to a mobile computing device such as a smartphone, tablet computer, or smart watch. In this example implementation, the computing device outputs content to its local display and/or speaker(s). In another example implementation, the computing device outputs content to an external display device (e.g., over Wi-Fi) such as a TV or an external computing system.

In example implementations of the disclosed technology, a computing device includes any number of hardware and/or software applications that are executable to facilitate any of the operations. In example implementations, one or more I/O interfaces facilitate communication between the computing device and one or more input/output devices. For example, a universal serial bus port, a serial port, a disk drive, a CD-ROM drive, and/or one or more user interface devices, such as a display, keyboard, keypad, mouse, control panel, touch screen display, microphone, etc., can facilitate user interaction with the computing device. The one or more I/O interfaces can be utilized to receive or collect data and/or user instructions from a wide variety of input devices. Received data can be processed by one or more computer processors as desired in various implementations of the disclosed technology and/or stored in one or more memory devices.

One or more network interfaces can facilitate connection of the computing device inputs and outputs to one or more suitable networks and/or connections; for example, the connections that facilitate communication with any number of sensors associated with the system. The one or more network interfaces can further facilitate connection to one or more suitable networks; for example, a local area network, a wide area network, the Internet, a cellular network, a radio frequency network, a Bluetooth enabled network, a Wi-Fi enabled network, a satellite-based network any wired network, any wireless network, etc., for communication with external devices and/or systems.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, implementations of the disclosed technology may provide for a computer program product, including a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

Certain implementations of the disclosed technology are described above with reference to mobile computing devices. Those skilled in the art recognize that there are several categories of mobile devices, generally known as portable computing devices that can run on batteries but are not usually classified as laptops. For example, mobile devices can include, but are not limited to portable computers, tablet PCs, Internet tablets, PDAs, ultra-mobile PCs (UMPCs) and smartphones.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "one implementation," "an implementation," "example implementation," "various implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

An embodiment of the present disclosure may be implemented according to at least the following:

Clause 1: A method of synthesis of a nucleotide chain, the nucleotide chain including an ordered plurality of nucleotides, the method comprising: identifying a first nucleotide of the ordered plurality of nucleotides; controlling a polymerase enzyme to assemble the first nucleotide onto the nucleotide chain by electrically modulating an electrode; identifying a subsequent nucleotide in the ordered plurality of nucleotides as a current nucleotide; and controlling the polymerase enzyme to assemble the current nucleotide onto an end of the nucleotide chain by electrically modulating the electrode.

Clause 2: The method of clause 1 further comprising: controlling the polymerase enzyme to assemble a telomere by electrically modulating the electrode, the polymerase enzyme assembling the first nucleotide onto an end of the telomere.

Clause 3: The method of clauses 1 or 2 further comprising: repeatedly identifying a subsequent nucleotide in the ordered plurality of nucleotides as the current nucleotide and controlling the polymerase enzyme to assemble the current nucleotide onto the end of the nucleotide chain until the polymerase enzyme assembles a complete nucleotide chain.

Clause 4: The method of any of clauses 1-3 further comprising, after assembly of the complete nucleotide chain, controlling the polymerase enzyme to assemble a telomere to the end of the complete nucleotide chain by electrically modulating the electrode.

Clause 5: The method of any of clauses 1-4 further comprising receiving data indicative of an order of nucleotides, the first nucleotide and subsequent nucleotide being identified from the data.

Clause 6: The method of clause 5 further comprising: dividing the order of nucleotides into a first sub-order comprising a plurality of nucleotides and a second sub-order comprising a plurality of nucleotides; assembling a first nucleotide chain fragment corresponding to the first sub-order; assembling a second nucleotide chain fragment corresponding to the second sub-order; and combining the first nucleotide chain fragment and the second nucleotide chain fragment.

Clause 7: The method of clause 6, wherein assembling the first nucleotide chain fragment comprises: identifying a first nucleotide of the first sub-order plurality of nucleotides; controlling a first polymerase enzyme to assemble the first nucleotide of the first sub-order onto the first nucleotide chain fragment by electrically modulating a first electrode; identifying a subsequent nucleotide of the first sub-order plurality of nucleotides as a current nucleotide of the first sub-order; and controlling the first polymerase enzyme to assemble the current nucleotide of the first sub-order onto an end of the first nucleotide chain fragment by electrically modulating the first electrode.

Clause 8: The method of clauses 6 or 7, wherein assembling the second nucleotide chain fragment comprises: identifying a first nucleotide of the second sub-order plurality of nucleotides; controlling a second polymerase enzyme to assemble the first nucleotide of the second sub-order onto the second nucleotide chain fragment by electrically modulating a second electrode; identifying a subsequent nucleotide of the second sub-order plurality of nucleotides as a current nucleotide of the second sub-order; and controlling the second polymerase enzyme to assemble the current nucleotide of the second sub-order onto an end of the first nucleotide chain fragment by electrically modulating the second electrode.

Clause 9: The method of any of clauses 6-8, wherein assembling the first nucleotide chain fragment and assembling the second nucleotide chain fragment are performed at least partially in parallel.

Clause 10: The method of any of clauses 7-9, wherein the first electrode and the second electrode are a part of a same electrode array.

Clause 11: The method of any of clauses 1-10, wherein controlling the polymerase enzyme to assemble the first nucleotide further comprises modulating a light source shining on the polymerase enzyme.

Clause 12: The method of any of clauses 1-11, wherein the polymerase enzyme is immobilized adjacent to the electrode.

Clause 13: The method of any of clauses 1-12, wherein the polymerase enzyme is leashed to the electrode with a polyethylene glycol (PEG) chain.

Clause 14: The method of any of clauses 1-13, wherein the polymerase enzyme is in a solution comprising nucleoside triphosphate.

Clause 15: The method of clause 14, wherein the solution further comprises magnesium chloride, a reaction buffer, or both magnesium chloride and a reaction buffer.

Clause 16: The method of any of clauses 1-15, wherein electric modulation comprises applying a series of voltage changes to the electrode.

Clause 17: The method of any of clauses 1-16, wherein the polymerase enzyme is a template-independent DNA polymerase.

Clause 18: The method of any of clauses 1-17, wherein each nucleotide of the ordered plurality of nucleotides comprises one from among adenine (A), thymine (T), guanine (G), and cytosine (C).

Clause 19: The method of clause 18, wherein controlling the polymerase enzyme to assemble A, T, G, or C to the end of the nucleotide chain requires distinct electrical modulation of the electrode.

Clause 20: A system comprising: an electrode; a polymerase enzyme immobilized adjacent to the electrode; and a processor; and a memory having stored thereon instructions that, when executed by the processor, control the processor to electrically modulate the electrode to control the polymerase enzyme to assemble a nucleotide chain, the nucleotide chain comprising an ordered plurality of nucleotides.

Clause 21: The system of clause 20, wherein the instructions, when executed by the processor, further control the processor to: identify a first nucleotide of the ordered plurality of nucleotides; control the polymerase enzyme to assemble the first nucleotide onto the nucleotide chain by electrically modulating an electrode; identify a subsequent nucleotide in the ordered plurality of nucleotides as a current nucleotide; and control the polymerase enzyme to assemble the current nucleotide onto an end of the nucleotide chain by electrically modulating the electrode.

Clause 22: A system comprising: an electrode; a polymerase enzyme immobilized adjacent to the electrode; and a processor; and a memory having stored thereon instructions that, when executed by the processor, control the processor to perform the method of any of clauses 1-19.

Clause 23: A non-transitory computer readable medium comprising program instructions for performing the method of any of clauses 1-19.

What is claimed is:

1. A method of de novo nucleotide chain assembly comprising:
    immobilizing a template-independent enzyme to an electrode platform comprising an electrode with a seeded inert surface functionalized with one or more links, the template-independent enzyme immobilized to the electrode platform via one or more of the links;
    controlling, via direct electrical-field modulation, the immobilized template-independent enzyme to assemble a first nucleotide of a nucleotide chain by electrically modulating the electrode; and
    controlling, via direct electrical-field modulation, the immobilized template-independent enzyme to assemble a next nucleotide of the nucleotide chain by electrically modulating the electrode;
    wherein the assembly of the nucleotide chain is a de novo assembly of the nucleotide chain without using primer and without using template enzymes.

2. A method of de novo deoxyribonucleic acid (DNA) synthesis comprising:
    receiving data indicative of a sequential order of a number (N) of nucleotides forming a nucleic acid sequence to be assembled, the sequential order of the nucleotides forming the nucleic acid sequence including N nucleotides from a first nucleotide, one or more intermediate nucleotides, and to a last nucleotide;
    attaching one or more template-independent DNA polymerases to an electrode platform comprising one or more electrodes, one or more of the electrodes having a seeded inert surface functionalized with one or more bio-links, one or more of the template-independent DNA polymerases attached to the electrode platform via one or more of the bio-links;
    controlling, via direct electrical-field modulation, one or more of the attached template-independent DNA polymerases to assemble the first nucleotide of the nucleic acid sequence by electrically modulating one or more of the electrodes to assemble the first nucleotide of the nucleic acid sequence; and
    repeating N−1 times:
        identifying a subsequent nucleotide in the sequential order of nucleotides as a current nucleotide; and
        controlling, via direct electrical-field modulation, one or more of the attached template-independent DNA polymerases to assemble the current nucleotide onto an end of the nucleic acid sequence by electrically modulating one or more of the electrodes to assemble the current nucleotide onto the nucleic acid sequence;
    until one or more of the attached template-independent DNA polymerases assembles a complete nucleic acid sequence comprising the sequential order of the nucleotide;
    wherein a subset of two or more electric modulations, from a set containing all of the electric modulations, is selected from a group consisting of a subset of electric modulations each at the same electric modulation, a subset of electric modulations of which at least two are at a different electric modulation one from another, a subset of electric modulations of which each are at a different electric modulation one from the others, and a combination thereof;
    wherein the synthesis of the nucleic acid sequence is a de novo synthesis of the nucleic acid sequence without using primer and without using template DNA polymerases.

3. The method of claim 2, further comprising, after assembly of the complete nucleic acid sequence, controlling, via direct electrical-field modulation, one or more of the attached template-independent DNA polymerases to assemble a telomere to an end of the complete nucleic acid sequence.

4. The method of claim 2, wherein at least one of the electrodes having the seeded inert surface functionalized with one or more of the bio-links is an electrode with:
    a plating of the inert surface to limit unintended chemical reactions;
    a coating of silica nanoparticles as a seeding layer; and
    at least one bio-link selected from the group consisting of a biotin-streptavidin bio-link and a biotin polyethylene glycol (PEG) silane bio-link.

5. The method of claim 4 further comprising:
    dividing the sequential order of the nucleotides into a first sub-order of nucleotides and a second sub-order of nucleotides;
    assembling a first nucleotide chain fragment of the complete nucleic acid sequence corresponding to the first sub-order;

assembling a second nucleotide chain fragment of the complete nucleic acid sequence corresponding to the second sub-order; and combining the first nucleotide chain fragment and the second nucleotide chain fragment to form the complete nucleic acid sequence.

6. The method of claim 5, wherein assembling the first nucleotide chain fragment and assembling the second nucleotide chain fragment are performed at least partially in parallel.

7. The method of claim 2, wherein the electrode platform comprises two or more electrodes that are a part of a same electrode array.

8. The method of claim 2, wherein controlling one or more of the attached template-independent DNA polymerases to assemble the first nucleotide comprises modulating a light source shining on one or more of the attached template-independent DNA polymerases at the first electric modulation.

9. The method of claim 2, wherein the attaching comprises immobilizing adjacent to an electrode providing the electrical-field modulation.

10. The method of claim 9, wherein the immobilizing comprises leashing to the electrode with a polyethylene glycol (PEG) chain.

11. The method of claim 4 further comprising:

forming the at least one electrode comprising the seeded inert surface functionalized with the one or more of the bio-links by:

plating the electrode with gold; and applying the silica nanoparticles through a self-assembled monolayer of (3-mercaptopropyl) trimethoxysilane;

wherein at least one of the bio-links is selected from the group consisting of a biotin-streptavidin bio-link and a biotin PEG silane bio-link.

12. The method of claim 11, wherein the forming further comprises:

depositing a thin-film sol-gel silica layer and/or an organosilane layer on the self-assembled monolayer.

* * * * *